United States Patent
Kobayashi et al.

(12) 
(10) Patent No.: US 6,531,433 B1
(45) Date of Patent: Mar. 11, 2003

(54) NON-AQUEOUS SCRUB COMPRISING WATER SOLUBLE CARBOHYDRATES

(75) Inventors: Masaru Kobayashi, Woodstock, CT (US); Takako Wright, Farmersville, TX (US); Shigeru Kishida, Stors, CT (US)

(73) Assignee: Abyssal Cosmetics, Inc., Richardson, TX (US)

( * ) Notice: Subject to any disclaimer, the term of this patent is extended or adjusted under 35 U.S.C. 154(b) by 41 days.

(21) Appl. No.: 09/643,173

(22) Filed: Aug. 21, 2000

(51) Int. Cl.⁷ .................................................. A61K 7/50
(52) U.S. Cl. ........................ 510/130; 510/119; 510/139; 510/470; 510/474; 424/70.1
(58) Field of Search ................................ 510/119, 130, 510/470, 424, 139; 424/70.1

(56) References Cited

U.S. PATENT DOCUMENTS

| | | | | |
|---|---|---|---|---|
| 4,673,526 A | * | 6/1987 | Zabotto et al. | 252/174.16 |
| 5,360,824 A | * | 11/1994 | Barker | 424/68 |
| 5,455,025 A | * | 10/1995 | Pereira et al. | 424/59 |
| 5,801,134 A | * | 9/1998 | Righton | 510/130 |
| 6,025,431 A | * | 2/2000 | Cardinali et al. | 524/547 |
| 6,221,826 B1 | | 4/2001 | Surutzidis et al. | 510/349 |

* cited by examiner

*Primary Examiner*—Necholus Ogden
(74) *Attorney, Agent, or Firm*—Eugene C. Rzucidlo

(57) ABSTRACT

A non-aqueous personal scrubbing composition comprising at least one water-soluble carbohydrate having a mean particle size diameter from about 100 microns to about 2000 microns in an amount from about 10 to about 90 weight percent of the total composition and non-aqueous media in an amount from about 10 to about 90 weight percent of the total composition.

4 Claims, No Drawings

NON-AQUEOUS SCRUB COMPRISING WATER SOLUBLE CARBOHYDRATES

FIELD OF THE INVENTION

The present invention relates to scrubbing formulations and more particularly to non-aqueous scrubbing formulations that are useful for personal skin care.

PRIOR ART

Personal scrubbing products have been used to smooth skin surface by removing excessive dead surface cells on the stratum corneum and to temporary improve blood circulation by physical abrasion. A wide variety of scrubbing products are sold in the marketplace. Usually scrubbing products contain abrasive particles of water-insoluble polymeric materials or water-soluble inorganic salts.

In personal scrubbing products, water-insoluble polymeric materials are used in aqueous or non-aqueous media or emulsions. However, all aqueous based scrubbing products tend to dry out the skin. Water-insoluble polymeric materials in aqueous media are not exception, they give scratching feeling during use and sometimes irritate skin and leave dry feel. Products in which polymeric materials are in non-aqueous media or emulsion give slightly less scratching feel because of reduced friction due to oily materials and do not leave dry feel on the skin. However, they are still too abrasive to some people.

Use of water-insoluble polymeric materials that are collapsible at relatively low shear force in scrubbing products has been suggested. The collapsible polymeric materials slightly reduce scratching feeling during use; however, they are still too abrasive to some people even in non-aqueous media or emulsion.

Use of water-soluble inorganic salts was proposed to solve the problem of being too abrasive. Water-soluble inorganic salts are usually in non-aqueous media or emulsion. Because of its solubility in water, water-soluble inorganic salts do not give scratching feel when used with water. When placed in non-aqueous phase of emulsion; however, water-soluble inorganic salts tend to migrate from non-aqueous phase to aqueous phase where they dissolve over period of time. To solve this problem, water-soluble inorganic salts are often placed in non-aqueous media. However, tendency of salts to settle to the bottom and difficulty in resuspending salts once settled due to the high density (e.g. densities are: sodium chloride: 2.165, sodium bicarbonate: 2.159, sodium sesquicarbonate: 2.112) made difficult to use this type of products.

SUMMARY OF THE INVENTION

The object of the present invention is to provide personal scrubbing compositions that are not too abrasive and do not leave scratching feel during and after use. Another objective of the present invention is to provide personal scrubbing compositions that are easy to use (including resuspendability). These objectives can be met by using water-soluble carbohydrates and non-aqueous media.

DETAILED DESCRIPTION OF THE INVENTION

While vigorous rubbing of the skin helps to remove excessive dead surface cells it may remove too much oil from the surface, leaving it feeling dry and rough. Because the personal scrubbing compositions of the present invention are non-aqueous base, the compositions minimize unpleasant scratching feeling and dryness of the skin, which is associated with most aqueous base scrubbing products, and help skin to soothe and comfort.

The personal scrubbing compositions of the present invention are highly effectual in scrubbing the skin without causing negative effects of being too abrasive, causing irritation on the skin, or leaving the skin dry. The scrubbing compositions of the present invention do not contain water; therefore, water-soluble carbohydrates dispersed in non-aqueous media in which said carbohydrates are insoluble to slightly soluble are stable. When the scrubbing compositions of the present invention are used with water, water-soluble carbohydrates are readily dissolved in water. Therefore, the scrubbing effect can be adjusted by the amount of water used with the scrubbing compositions of the present invention; from very abrasive when no water is used to least abrasive when large amount of water is used. Scrubbing effect can be further adjusted by use of warm water which increases the solubility of water-soluble carbohydrates.

Substances having solubilities (at 25°C.) of less than 0.1 gram per liter of solvent are defined insoluble. Substances having solubilities (at 25° C.) of more than 10 grams per liter of solvent are defined soluble. Substances having solubilities (at 25° C.) of 0.1 to 10 grams per liter of solvent are defined slightly soluble.

The scrubbing compositions of the present invention comprise from about 10 to about 90 weight percent of water-soluble carbohydrates and from about 10 to about 90 weight percent of non-aqueous media in which the water-soluble carbohydrates are insoluble to slightly soluble.

Water-soluble carbohydrates used in the present invention are monosaccharides, disaccharides, and polysaccharides. Monosaccharides are any simple sugars having the formula $C_6H_{12}O_6$ including glucose, fructose, and galactose. Disaccharides are ethers formed from two monosaccharides and include sucrose, maltose, cellobiose, and lactose. Polysaccharides are polyethers of monosaccharides. Polysaccharides may be used in the present invention include starches, such as amylose and amylopectin, glycogen, but do not include dextran or cellulose because of water insolubility.

Water-soluble carbohydrates have relatively low density (sucrose: 1.587, glucose: 1.544) thus are easily dispersed in non-aqueous media without being settled fast at the bottom. Also, water-soluble carbohydrates are easy to resuspend in non-aqueous media once settled at the bottom.

The said water-soluble carbohydrates have a mean particle size diameter from about 100 microns to about 2,000 microns. It is found that water-soluble carbohydrates having a mean particle size diameter greater than about 2,000 microns take extended period of time to dissolve even when used with warm water and thus are too abrasive. It is also found that water-soluble carbohydrates having a mean particle size diameter less than about 100 microns are less effective for providing scrubbing effect.

Non-aqueous media used in the present invention are materials in which water-soluble carbohydrates are insoluble or slightly soluble. Non-aqueous media may be one or combination of two or more materials selected from oils, fats, hydrocarbons, polyols, silicones, esters, ethers, fatty acids, fatty alcohols, alcohols, waxes and other cosmetically acceptable non-aqueous materials.

Oils and fats include plant oils, such as almond oil, apricot kernel oil, avocado oil, camellia oil, candlenut oil, canola (rapeseed) oil, carrot oil, cashew nut oil, castor oil, corn oil, cottonseed oil, cucummber oil, evening primrose oil, grape seed oil, hazelnut oil, kiwi seed oil, A macadamia nut oil, meadowfoam seed oil, passion flower oil, peach kernel oil, peanut oil, pecan oil, pumpkin seed oil, rice oil, rose hips oil, safflower oil, soybean oil, sesame oil, sunflower oil, tomato oil, wheat germ oil, olive oil, and other cosmetically acceptable plant oils, plant fats, such as cacao butter, shea butter, Japan wax, coconut oil, palm oil, palm kernel oil and other cosmetically acceptable plant fats, animal oils and fats, such as cod liver oil, egg oil, emu oil, fish liver oil, milk fat, mink oil, tallow, turtle oil and other cosmetically acceptable animal oils and fats.

Hydrocarbons include butane, isoparaffin, cyclohexane, dioctylcyclohexane, dipentene, isobutane, isododecane, isoeicosane, isohexadecane, isopentane, mineral oil, mineral spirits, paraffin, pentane, petrolatum, squalane, squalene, and other cosmetically acceptable hydrocarbons.

Polyols include ascorbic acid, ascorbyl dipalmitate, ascorbyl palmitate, ascorbyl stearate, diglycerin, erythritol, glycerin, polyglucuronic acid, polyglycerin, and other cosmetically acceptable polyols.

Silicones include cyclomethicone, dimethicone, dimethicone copolyol, methicone, phenyl dimethicone, phenyl methicone, phenyl trimethicone, and other cosmetically acceptable silicones.

Esters include butyl esters, such as butyl, isbstearate, butyl myristate, and butyl oleate, cetyl esters, such as cetyl lactate, cetyl laurate, cetyl myristate, cetyl octanoate, cetyl oleate, cetyl palmtate, cetyl ricinoleate, and cetylstearate, decyl esters, diethyl esters, isoctyl esters, isodecyl esters, isopropyl esters, isostearyl esters, jojoba esters, octyldodecyl esters, such as D octyldodecyl oleate, octyidodecyl behenate, octyldodecyl benzoate, octyidodecyl erucate, octyldodecyl lactate, octyldodecyl myristate, octyidodecyl neodecanoate, octyldodecyl neopentanoate, octyldodecyl.octanoate, octyldodecyl oleate, octyidodecyl ricinoleate, octyldodecyl stearate, and octyidodecyl stearoyl stearate, octyl esters, such as octyl isopalmitate, octyl isostearate, octyl laurate, octyl myristate, octyl neopentanoate, octyl octanoate, octyl oleate, and octyl palmitate, polyvinyl acetate, propylene glycol esters, and other cosmetically acceptable esters.

Ethers include butoxypropanol, capsaicin, carboxymethyl chitin, diethylene glycol, diglycerin, dimethyl ether, dipropylene glycol, ethoxyethanol, ethylcellulose, eucalyptol, eugenol, ferulic acid, isoeugenol, methoxyethanol, methyl eugenol, methy hexyl ether, octoxyglyceryl behenate, octoxyglyceryl palmitate, phenoxyethanol, polyglycerin, polyglyceryl ethers, such as polyoxypropylene diglyceryl ether, polyvinyl methyl ether, polyvinyl stearyl ether, propylene glycol myristyl ether, triclosan, and other cosmetically acceptable ethers.

Fatty acids include arachidic acid, arachidonic acid, beeswax acid, behenic acid, capric acid, caproic acid, caprylic acid, coconut acid, corn acid, cottonseed acid, hydroxystearic acid, isostearic acid, lauric acid, linoleic acid, linolenic acid, linseed acid, myristic acid, oleic acid, palm acid, palmitic acid, ricinoleic acid, soy acid, stearic acid, tallow acid, wheat germ acid, and other cosmetically acceptable fatty acids.

Alcohols and fatty alcohols include abietyl alcohol, arachidyl alcohol, behenyl alcohol, butylene glycol, caprylic alcohol, cetearyl alcohol, cetyl alcohol, decyl alcohol, lauryl alcohol, lauryl alcohol, myristyl alcohol, oleyl alcoho, palm, alcohol, propylene glycol, stearyl alcohol, and other cosmetically acceptable alcohols and fatty alcohols.

Waxes include beeswax, candelilla wax, jpjoba wax, lanolin, orange peel wax, rice wax, shellac wax, synthetic wax, and other cosmetically acceptable waxes.

EXAMPLES

The following examples further illustrate the invention but are not intended to limit its scope.

Example 1

A scrubbing composition was prepared by combining the following ingredients using conventional mixing techniques.

| Ingredients | Weight Percent |
| --- | --- |
| Octyldodecyl Oleate | 50 |
| Sucrose | 50 |

The mean particle size of sucrose used was approximately 490 micron. When this composition was used on the skin it provided scrubbing effect. When this composition was used with warm water on the face, it provided scrubbing effect but did not leave scratching feeling. After granules of sucrose were settled to the bottom, it was easily resuspended for use.

Comparative Example 1

A scrubbing composition was prepared by combining the following ingredients using conventional mixing techniques.

| Ingredients | Weight Percent |
| --- | --- |
| Octyldodecyl Oleate | 60 |
| Polyethylene bead (collapsible) | 40 |

The mean particle size of collapsible polyethylene bead used was approximately 450 micron. When this composition was used on the skin, it provided scrubbing effect. However, the product left scratching feeling. After polyethylene beads were settled to the bottom, it was easily resuspended for use.

Comparative Example 2

A scrubbing composition was prepared by combining the following ingredients using conventional mixing techniques.

| Ingredients | Weight Percent |
| --- | --- |
| Octyldodecyl Oleate | 50 |
| Sodium Chloride | 50 |

The mean particle size of sodium chloride used was approximately 400 micron. When this composition was used on the skin, it provided scrubbing effect. When this composition was used with warm water on the face, it provided scrubbing effect but did not leave scratching feeling. After granules of sodium chloride were settled to the bottom, it was not easily resuspended for use.

What is claimed:

1. A non-aqueous personal scrubbing composition comprising:

(a) at least one water-soluble carbohydrate having a mean particle size diameter from about 100 microns to about 2000 microns in an amount from about 10 to about 90 weight percent of the total composition, wherein the at least one water-soluble carbohydrate is a monosaccharide, or a disaccharide, and (b) non-aqueous media in an amount from about 10 to about 90 weight percent of the total composition.

2. The non-aqueous scrubbing composition according to claim 1, wherein said non-aqueous media are those in which the at least one carbohydrate is insoluble or slightly soluble at room temperature.

3. A non-aqueous personal scrubbing composition consisting essentially of:

(a) at least one water-soluble carbohydrate having a mean particle size diameter from about 100 microns to about 2000 microns in an amount from about 10 to about 90 weight percent of the total composition, and (b) non-aqueous media in an amount from about 10 to about 90 weight percent of the total composition; wherein said at least one water-soluble carbohydrate is a monosaccharide or a disaccharide.

4. The non-aqueous scrubbing composition according to claim 3, wherein said non-aqueous media are those in which the at least one carbohydrate is insoluble or slightly soluble at room temperature.

* * * * *